United States Patent
Vidal et al.

(10) Patent No.: US 6,231,623 B1
(45) Date of Patent: May 15, 2001

(54) METHODS OF DYEING KERATIN FIBERS WITH COMPOSITIONS CONTAINING PYRAZOLO-AZOLE COUPLERS

(75) Inventors: Laurent Vidal, Paris; Gérard Malle, Rungis; Eric Monteil, Vincennes, all of (FR)

(73) Assignee: L'Oreal S.A. (FR)

( * ) Notice: Subject to any disclaimer, the term of this patent is extended or adjusted under 35 U.S.C. 154(b) by 0 days.

(21) Appl. No.: 09/155,212

(22) PCT Filed: Mar. 21, 1997

(86) PCT No.: PCT/FR97/00507

§ 371 Date: Apr. 30, 1999

§ 102(e) Date: Apr. 30, 1999

(87) PCT Pub. No.: WO97/35551

PCT Pub. Date: Oct. 2, 1997

(30) Foreign Application Priority Data

Mar. 22, 1996 (FR) .................................................. 96 03626

(51) Int. Cl.⁷ .................................................. A61K 7/13
(52) U.S. Cl. .................................. 8/409; 8/423; 8/573
(58) Field of Search .............................. 8/409, 423, 573

(56) References Cited

U.S. PATENT DOCUMENTS

| | | | |
|---|---|---|---|
| 3,061,432 | 10/1962 | Menzel et al. | 430/376 |
| 3,227,554 | 1/1966 | Barr et al. | 430/382 |
| 3,419,391 | 12/1968 | Young | 430/387 |
| 3,725,067 | 4/1973 | Bailey et al. | 430/476 |
| 3,820,948 | 6/1974 | Berth | 8/409 |
| 3,926,631 | 12/1975 | Arai et al. | 430/226 |
| 4,128,425 | 12/1978 | Greenwald | 430/440 |
| 4,293,543 | 10/1981 | Cotte et al. | 8/405 |
| 4,500,630 | 2/1985 | Sato et al. | 430/386 |
| 4,621,046 | * 11/1986 | Sato et al. | 430/381 |
| 5,256,526 | 10/1993 | Suzuki et al. | 430/384 |
| 5,380,340 | * 1/1995 | Neunhoeffer et al. | 8/409 |
| 5,441,863 | 8/1995 | Tang et al. | 430/558 |
| 5,457,210 | 10/1995 | Kim et al. | 548/262.4 |

FOREIGN PATENT DOCUMENTS

| | | |
|---|---|---|
| 2 160 317 | 6/1973 | (DE) . |
| 2 359 999 | 6/1975 | (DE) . |
| 3 731 395 | 4/1989 | (DE) . |
| 3 843 892 | 6/1990 | (DE) . |
| 4 009 097 | 9/1991 | (DE) . |
| 4 133 957 | 4/1993 | (DE) . |
| 0 030 680 | 6/1981 | (EP) . |
| 0 119 860 | 9/1984 | (EP) . |
| 0 285 274 | 10/1988 | (EP) . |
| 0 304 001 | 2/1989 | (EP) . |
| 0 309 652 | 4/1989 | (EP) . |
| 0 320 764 | 6/1989 | (EP) . |
| 0 456 226 | 11/1991 | (EP) . |
| 0 488 248 | 6/1992 | (EP) . |
| 0 488 909 | 6/1992 | (EP) . |
| 0 518 238 | 12/1992 | (EP) . |
| 0 547 864 | 6/1993 | (EP) . |
| 0 557 851 | 9/1993 | (EP) . |
| 0 578 248 | 1/1994 | (EP) . |
| 0 591 103 | 4/1994 | (EP) . |
| 1 564 999 | 4/1969 | (FR) . |
| 2 075 583 | 10/1971 | (FR) . |
| 2 466 492 | 4/1981 | (FR) . |
| 2 486 913 | 3/1987 | (FR) . |
| 1 026 978 | 3/1963 | (GB) . |
| 1 153 196 | 6/1966 | (GB) . |
| 1 458 377 | 9/1974 | (GB) . |
| 58-42045 | 3/1983 | (JP) . |
| 59-99437 | 6/1984 | (JP) . |
| 59-162548 | 9/1984 | (JP) . |
| 59-171956 | 9/1984 | (JP) . |
| 60-33552 | 2/1985 | (JP) . |
| 60-43659 | 3/1985 | (JP) . |
| 60-172982 | 6/1985 | (JP) . |
| 60-190779 | 9/1985 | (JP) . |
| 62-279337 | 12/1987 | (JP) . |
| 63-169571 | 7/1988 | (JP) . |

(List continued on next page.)

OTHER PUBLICATIONS

R. Stollé, "Ueber die Ueberführung der secundären Säurehydrazide in Derivate des Furodiazols, Pyrrodiazols und Thiodiazols", Chemischen Gesellschaft, pp. 797–798, 1899.

(List continued on next page.)

Primary Examiner—Caroline D. Liott
(74) Attorney, Agent, or Firm—Finnegan, Henderson, Farabow, Garrett & Dunner, L.L.P.

(57) ABSTRACT

The present invention relates to a composition for dyeing keratinous fibers, especially human hair, which in a medium appropriate for dyeing comprises:

as coupler at least one compound of formula:

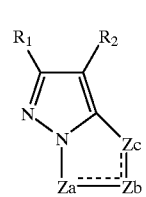

(I)

in which:

$R_1$ is especially hydrogen, alkyl, aryl, a heterocycle, a halogen, etc.;

$R_2$ is especially hydrogen, halogen, aryloxy, alkoxy, acyloxy, arylthio, alkylthio, heteroarylthio, heteroaryloxy, etc.;

$Z_a$, $Z_b$ and $Z_c$ are independently a nitrogen atom or a carbon which carries a radical $R_3$ or $R_4$ whose meanings are identical to those of $R_1$; at least one of $Z_a$, $Z_b$ and $Z_c$ is a nitrogen atom; and $R_3$ and $R_4$ may together form an unsubstituted or substituted aromatic ring; and at least one oxidation base.

32 Claims, No Drawings

FOREIGN PATENT DOCUMENTS

| | | |
|---|---|---|
| 62-36011 | 8/1994 | (JP) . |
| 7-36159 | 2/1995 | (JP) . |
| 7-84348 | 3/1995 | (JP) . |
| 7-92632 * | 4/1995 | (JP) . |
| WO 92/04349 * | 3/1992 | (WO) . |
| WO 92/04883 * | 4/1992 | (WO) . |
| WO 94/04130 * | 3/1994 | (WO) . |
| WO 94-89970 * | 4/1994 | (WO) . |
| WO 94/08959 * | 4/1994 | (WO) . |
| WO 94/08969 * | 4/1994 | (WO) . |

OTHER PUBLICATIONS

Hans Beyer et al., "Über die Pyrazolbildung aus α–Chlor–acetessigester und Thiocarbohydazid", Chemische Berichte, pp. 2550–2555, 1956.

H. Wilde et al., Synthese von 4H–Pyrazolo[1,5–a]benzimidazolen, Journal Für Praktische Chemie, pp. 829–836, 1984.

Lidia Wyzgowska et al., "O Reakcjach Trikarboetoksymetanu VIII", Acta Poloniae Pharmaceutica, pp. 83–88, 1982.

E. Hannig et al., "Zur Kenntnis des 4–aminierten Phenylbutazons", Die Pharmazie, pp. 231, 1980.

Giuliana Cardillo et al., "Su due constituenti minori della Kamala", Gazetta Chimica Italiana, pp. 725–734, 1965.

Thomas Kauffmann et al., Synthese von Amidrazonon aus Nitrilen und Natriumhydrazid, pp. 3436–3443, 1964.

von Helmut Dorn et al., "Synthese und Methylierung von 1H–Pyrazolo[3,4–b]pyrazinen, einer neuen Klasse von Purin–Antagonisten", Annalen der Chemie, pp. 118–123, 1968.

von Helmut Dorn et al., "Über die elektrophile Substitution von 3(5)–Amino–pyrazol", Annalen der Chemie, pp. 141–146, 1967.

Mohamed Helmi Elnagdi et al., "Studies on 3,5–pyrazolidinediones. IV. Addition of 4–Arylazo–3,5–pyrazolidinesdiones to Ethyl Acrylate", Bulletin of Them Chemical Society of Japan, vol. 46, pp. 1830–1833, 1973.

Günther Ege et al., "A Simple Synthesis of 3(5)–Aminopyrazole", Angew. Chem. internat. Edit, vol. 13, No. 3, pp. 206–207, 1974.

Kazumasa Takahashi et al., "Syntheses of 3(5)–Substituted–4–(N–methylanilino)–5(3)–aminopyrazoles by Reaction of β–Hydroxy–α–cyano–enamines with Hydrazines", Journal of Synthetic Organic Chemistry, No. 8, pp. 794–796, 1985.

Chiara B. Vincentini et al., "Pyrazolo[3,4–d][1,2,3] Triazole–1–carboxamides and 5–Alkylaminopyrazolo[3,4–d]oxazoles: Synthesis and Evaluation of the in Vitro Antifungal Activity", II Farmaco, vol. 47, No. 7, 8, pp. 1021–1034, 1992.

Edward C. Taylor et al., "The Reaction of Malononitrile with Substituted Hydrazines: New Routes to 4–Aminopyrazolo[3,4–d]pyrimidines", Journal of the merican Chemical Society, vol. 81, No. 10, pp. 2456–2464, 1959.

C.B. Vincentini et al., "A New Fused Heterocyclic System; 6HPyrazolo[3,4–c][1,2,5]thiadizine 2,2–Dioxide", Journal of Heterocyclic Chemistry, vol. 26, No. 3, pp. 797–803, 1989.

E.J. Browne et al.,"Triazoles. Part VII. Syntheses of Substituted 1,2,4–Triazoles", Journal of The Chemical Society, pp. 5149–5152, 1962.

Philip Magnus et al., "Synthesis of helical Poly–β–pyrroles. Multiple Atropisomerism Resulting in Helical Enantiomorphic Conformations", Journal of the American Chemical Society, vol. 112, No. 6, pp. 2465–2468, 1990.

Paul Carter et al., "Studies on the Synthesis of the Antitumor Agent CC–1065. Synthesis of PDE I and PDE II, Inhibitors of Cyclic Adenosine–3,5–monophosphate Phosphodiesterase Using the 3,3–Bipyrrole Strategy", Journal of the American Chemical Society, vol. 109, No. 9, pp. 2711–2717, 1987.

H. Koopman, "Investigations on Herbicides IV, The synthesis of 2,6–dichlorobenzonitrile", Recueil, vol. 80, No. 9–10, pp. 1075–1083, 1961.

Joseph Bailey, "Synthesis of 1H–Pyrazolo[3,2–c]–s–Triazoles and Derived Azamethine Dyes", Journal of the Chemical Society, pp. 2047–2052, 1977.

Mohamed Helmy Elnagdi et al., "Routes for the Synthesis of 3,5–Diaminopyrazoles, 2–Aminopyrazolo[1,5–a]pyrimidines and 5–Aminopyrazolo[1,5–a]pyramidines", Journal f. prakt. chemie, Band 320, heft 4, pp. 533–538, 1978.*

* cited by examiner

METHODS OF DYEING KERATIN FIBERS WITH COMPOSITIONS CONTAINING PYRAZOLO-AZOLE COUPLERS

The invention relates to a composition for the oxidation dyeing of keratinous fibres, especially human hair, which comprises at least one pyrazolo-azole compound as coupler and at least one oxidation base.

It is known to dye keratinous fibres, and especially human hair, with dyeing compositions comprising oxidation dye precursors, especially ortho- or para-phenylenediamines, ortho- or para-aminophenols and heterocyclic compounds, which are referred to generally as oxidation bases. The oxidation dye precursors, or oxidation bases, are colourless or slightly coloured compounds which, when combined with oxidizing products, are able to give rise to coloured compounds and dyes by a process of oxidative condensation.

It is also known that the shades obtained with these oxidation bases can be varied by combining them with couplers or coloration modifiers, the latter being selected in particular from aromatic meta-diamines, meta-aminophenols, meta-diphenols and certain heterocyclic compounds, such as indole compounds.

The variety of molecules employed as oxidation bases and couplers makes it possible to obtain a wide range of colours.

The "permanent" coloration obtained by means of these oxidation dyes is required, moreover, to meet a certain number of requirements. Hence it must have no toxicological drawbacks, must allow shades of the desired intensity to be obtained, and must have good resistance to external agents (light, inclement weather, washing, permanent-waving, perspiration and friction).

The dyes must also allow white hair to be covered and, finally, they must be as unselective as possible; in other words, they must allow the smallest possible differences in coloration to be produced over the entire length of a single keratinous fibre, which may in fact be sensitized (i.e. damaged) differently between its tip and its root.

The Applicant has now discovered that it is possible to obtain new, powerful dyes, of low selectivity and particularly high resistance, which are capable of giving rise to intense colorations in various shades, using pyrazolo-azole compounds as couplers in the presence of an oxidation base.

It is this discovery which forms the basis of the present invention.

The invention provides a composition for dyeing keratinous fibres, and especially human keratinous fibres such as hair, which is characterized in that it comprises, in a medium appropriate for dyeing:

as coupler, at least one pyrazolo-azole compound of formula (I) or one of its addition salts with an acid:

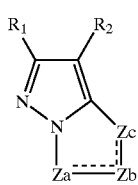

(I)

in which:

$R_1$ is: a hydrogen atom; a linear or branched $C_1$–$C_{20}$ alkyl radical which is optionally substituted by one or two radicals R selected from the group consisting of halogen, nitro, cyano, hydroxyl, alkoxy, aryloxy, amino, alkylamino, acylamino, carbamoyl, sulphonamido, sulphamoyl, imido, alkylthio, arylthio, aryl, alkoxycarbonyl and acyl; an aryl radical (such as phenyl or naphthyl) which is optionally substituted by one or two radicals R as defined above; a 5- or 6-membered heterocycle having at least one nitrogen, oxygen or sulphur atom (such as pyridyl, quinolyl, pyrrolyl, morpholyl, furyl, tetrahydrofuryl, pyrazolyl, triazolyl, tetrazolyl, triazolyl, oxazolyl, imidazolyl or thiadiazolyl) and being optionally substituted by one or two radicals R as defined above;

when $R_1$ is an alkyl radical, an aryl radical or a 5- or 6-membered heterocycle (as defined above) it can be attached to the carbon atom of the ring system by way of an oxygen, nitrogen or sulphur atom (in this case $R_1$ becomes $XR_1$ where X=O, NH, S);

$R_1$ may also be a halogen atom (such as bromine, chlorine or fluorine); an acyl radical; a sulphonyl radical; a sulphinyl radical; a phosphonyl radical; a carbamoyl radical; a sulphamoyl radical; a cyano radical; a siloxy radical; an amino radical; an acylamino radical; an acyloxy radical; a carbamoyloxy radical; a sulphonamide radical; an imide radical; a ureido radical; a sulphamoylamino radical; an alkoxycarbonylamino radical; an aryloxycarbonylamino radical; an alkoxycarbonyl radical; an aryloxycarbonyl radical; or a carboxyl radical;

$R_2$ is: a hydrogen atom; a halogen atom, such as bromine, chlorine or fluorine; an acetylamido group; an alkoxy radical (such as, for example: methoxy, ethoxy, propyloxy, benzyloxy, methoxyethoxy, phenoxyethoxy, 2-cyanoethoxy, phenethyloxy, p-chlorobenzyloxy or methoxyethylcarbamoylmethoxy); an aryloxy radical (such as, for example: phenoxy, 4-methoxyphenoxy, 4-nitrophenoxy, 4-cyanophenoxy, 4-methanesulphonamidophenoxy, 4-methanesulphonylphenoxy, 3-methylphenoxy or 1-naphthyloxy); an acyloxy radical (such as, for example: acetoxy, propanoyloxy, benzoyloxy, 2,4-dichorobenzoyloxy, ethoxyalkyloxy, pyruviloyloxy, cinnamoyloxy or myristoyloxy); an arylthio radical (such as, for example: phenylthio, 4-carboxyphenylthio, 2-ethoxy-5-tert-butylphenylthio, 2-carboxyphenylthio or 4-methanesulphonylphenylthio); an alkythio radical (such as, for example: methylthio, ethylthio, propylthio, butylthio, 2-cyanoethylthio, benzylthio, phenethylthio, 2-(diethylamino)ethylthio, ethoxyethylthio or phenoxyethylthio); a heteroarylthio radical (such as, for example: 5-phenyl-2,3,4,5-tetrazolylthio or 2-benzothiazolylthio); a heteroaryloxy radical (such as, for example: 5-phenyl-2,3,4,5-tetrazolyloxy or 2-benzothiazolyloxy); a thiocyano radical; an N,N-diethylthiocarbonylthio radical; a dodecyloxythiocarbonylthio radical; a benzenesulphonamido radical; an N-ethyltoluenesulphonamido radical; a pentafluorobutanamido radical; a 2,3,4,5,6-pentafluorobenzamido radical; a p-cyanophenylureido radical, an N,N-diethylsulphamoylamino radical; a pyrazolyl radical; an imidazolyl radical; a triazolyl radical; a tetrazolyl radical; a benzimidazolyl radical; a 1-benzyl-5-ethoxy-3-hydantoinyl radical; a 1-benzyl-3-hydantoinyl radical; 5,5-dimethyl-2,4-dioxo-3-oxazolidinyl; a 2-oxy-1,2-dihydro-1-pyridinyl radical; an alkylamido; an arylamido; a radical $NR^{III}R^{IV}$ where $R^{III}$ and $R^{IV}$ are identical or different and are a $C_1$–$C_4$ alkyl; a hydroxyalkyl; a carboxyl; or an alkoxycarboxyl radical.

$Z_a$, $Z_b$ and $Z_c$ independently of one another are a nitrogen atom, a carbon atom carrying a radical $R_3$ or $R_4$ as defined for the radical $R_1$; with the proviso that at least one of the radicals $Z_a$, $Z_b$ and $Z_c$ is other than a carbon atom; $R_3$ and $R_4$ may also together form a substituted or unsubstituted aromatic ring such as phenyl;

and at least one oxidation base.

The acid addition salts of the compounds of the invention can be selected in particular from hydrochlorides, hydrobromides, tartrates, tosylates, benzenesulphonates, sulphates, lactates and acetates.

Among the radicals $R_1$ of the above-defined formula (I), preference is given to the radicals selected from the group consisting of: a hydrogen atom; a linear or branched $C_1$–$C_4$ alkyl; a phenyl; a phenyl substituted by a halogen atom, a $C_1$–$C_4$ alkyl, a $C_1$–$C_4$ alkoxy, a nitro group, an amino group, a trifluoromethyl group or $C_1$–$C_4$ alkylamino group; a benzyl radical; a benzyl radical substituted by a halogen atom, a $C_1$–$C_4$ alkyl, a $C_1$–$C_4$ alkoxy, a nitro group, an amino group or a trifluoromethyl group; a $C_1$–$C_4$ alkylamino; a heterocycle selected from thiophene, furan and pyridine; a trifluoromethyl radical; a radical $(CH_2)_p$—X—$(CH_2)_q$—OR' where p and q are identical or different integers from 1 to 3, R' is H or methyl and X is an oxygen atom or a group NR" where R" is hydrogen or methyl; a $C_1$–$C_4$ hydroxyalkyl; a $C_1$–$C_4$ aminoalkyl; a $C_1$–$C_4$ alkylamino; a $C_1$–$C_4$ dialkylamino; an arylamino; an alkoxy radical selected from methoxy, ethoxy and phenoxy; a halogen selected from fluorine, chlorine and bromine; a carboxyl group; a $C_1$–$C_4$ alkoxycarbonyl; a phenyloxycarbonyl; methylthio; ethylthio; phenylthio; methanesulphonyl; and cyano.

Among the radicals $R_1$ of the above-defined formula (I), particular preference is given to the radicals selected from the group consisting of: hydrogen; an alkyl selected from methyl, ethyl, isopropyl and tert-butyl; a halogen selected from fluorine and chlorine; phenyl; tolyl; 4-chlorophenyl; 4-methoxyphenyl; 3-methoxyphenyl; 2-methoxyphenyl; benzyl; a heterocycle selected from pyridyl, furyl and thienyl; trifluoromethyl; hydroxymethyl; aminomethyl; methoxy or ethoxy; methylamino or ethylamino or dimethylamino; carboxyl; methoxycarbonyl or ethoxycarbonyl; and cyano.

More particular preference is given to the radicals $R_1$ selected from the group consisting of: hydrogen; methyl; ethyl; phenyl; tolyl; 4-chlorophenyl; 4-methoxyphenyl; benzyl; trifluoromethyl; chloro; a methoxy or ethoxy radical; a carboxyl radical; methylamino or dimethylamino; and cyano.

Among the radicals $R_2$ of the above-defined formula (I), preference is given to the radicals selected from the group consisting of: a hydrogen atom; a $C_1$–$C_4$ alkoxy; phenoxy; phenoxy substituted by a halogen atom, a $C_1$–$C_4$ alkyl, a carboxyl or a trifluoromethyl group; an acyloxy radical; benzyloxy; $C_1$–$C_4$ alkylthio; phenylthio; phenylthio substituted by a halogen atom, a $C_1$–$C_4$ alkyl, a carboxyl or a trifluoromethyl group; a $C_1$–$C_4$ alkylamido; phenylamido; a radical $NR'''R^{IV}$ where $R'''$ and $R^{IV}$ are identical or different and are a $C_1$–$C_4$ alkyl or a $C_1$–$C_4$ hydroxyalkyl; a carboxyl; and a $C_1$–$C_4$ alkoxycarboxyl radical.

Among the radicals $R_2$ of the above-defined formula (I), particular preference is given to the radicals selected from the group consisting of: hydrogen; chlorine or bromine; methoxy or ethoxy; phenyloxy; 4-methylphenyloxy; acyloxy; benzyloxy; methylthio or ethylthio; phenylthio; 4-methylphenylthio; 2-tert-butylphenylthio; acetamido; phenylacetamido; dimethylamino; diethylamino; ethylmethylamino; and (β-hydroxyethyl)methylamino.

More particular preference is given to the radicals $R_2$ selected from the group consisting of: hydrogen; chlorine; ethoxy; phenoxy; benzyloxy; acyloxy; acetamido; and dimethylamino.

Among the radicals $R_3$ and $R_4$ of the above-defined formula (I) preference is given to the radicals selected from the group consisting of: a hydrogen atom; a linear or branched $C_1$–$C_4$ alkyl; a trifluoromethyl radical; a phenyl; a phenyl substituted by one or two groups selected from a halogen, a $C_1$–$C_4$ alkyl, a $C_1$–$C_4$ alkoxy, a hydroxyl, a carboxyl, a nitro group, a $C_1$–$C_4$ alkylthio, a methylenedioxy group, an amino group, a trifluoromethyl group or a $C_1$–$C_4$ alkylamino; a benzyl radical; a benzyl radical substituted by a halogen atom, a methyl or isopropyl, or methoxy; a $C_1$–$C_4$ hydroxyalkyl; a $C_1$–$C_4$ aminoalkyl; a $C_1$–$C_4$ alkylaminoalkyl; an alkoxy radical selected from methoxy, ethoxy and phenoxy; methylthio; ethylthio; phenylthio; methanesulphonyl; and a substituted or unsubstituted aromatic ring formed by $R_3$ and $R_4$, such as phenyl, phenyl substituted by a sulphonyl radical, a halogen, a $C_1$–$C_4$ alkoxy, a $C_1$–$C_4$ alkyl, nitro, cyano, amino, alkylamino or trifluoromethyl.

Among the radicals $R_3$ and $R_4$ of the above-defined formula (I) particular preference is given to the radicals selected from the group consisting of: hydrogen; an alkyl selected from methyl, ethyl, isopropyl, n-propyl and tert-butyl; phenyl; tolyl; 2-, 3- or 4-chlorophenyl; 3- or 4-hydroxyphenyl; 3- or 4-aminophenyl; 3- or 4-methoxyphenyl; 4-trifluoromethylphenyl; benzyl; trifluoromethyl; hydroxymethyl; hydroxyethyl; hydroxyisopropyl; aminomethyl or aminoethyl; methoxy or ethoxy; methylthio or ethylthio; a substituted or unsubstituted aromatic ring formed by $R_3$ and $R_4$, such as phenyl, tolyl, sulphonylphenyl or chlorophenyl.

More particular preference is given to the radicals $R_3$ and $R_4$ selected from the group consisting of: hydrogen; methyl; ethyl; isopropyl; phenyl; 4-chlorophenyl; 4-methoxyphenyl; 4-aminophenyl; methoxy or ethoxy; methylthio or ethylthio; and a phenyl ring formed by $R_3$ and $R_4$.

Among preferred compounds of the invention of formula (I), mention may be made of those selected from the group consisting of:

i) the pyrazolo[1,5-b]-1,2,4-triazoles of formula:

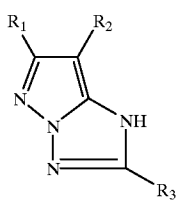
(Ia)

ii) the pyrazolo[3,2-c]-1,2,4-triazoles of formula:

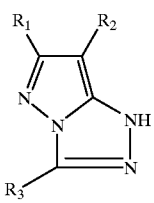
(Ib)

iii) the pyrazolotetrazoles of formula:

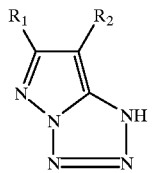
(Ic)

iv) the pyrazolo[1,5-a]imidazoles of formula:

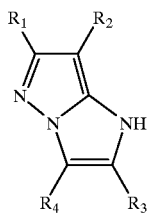
(Id)

v) the pyrazolo[5,1-e]pyrazoles of formula:

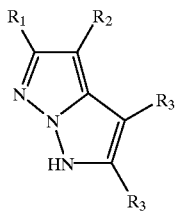
(Ie)

vi) the pyrazolo[5,1-e]-1,2,3-triazoles of formula:

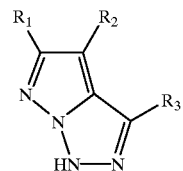
(If)

in which $R_1$, $R_2$, $R_3$ and $R_4$ are as defined above for the formula (I).

As examples of compounds of formula (Ia) or (Ib), particular mention may be made of those for which:

$R_1$ is hydrogen, methyl, ethylthio, amino, trifluoromethyl, carboxyl, phenyl, ethoxy or cyano;

$R_2$ is hydrogen or chlorine; and $R_3$ is hydrogen, methyl, ethyl, isopropyl, β-aminoethyl, β-hydroxyethyl, phenyl, methylthio or ethoxy.

Among the compounds of formula (Ia) above very particular mention may be made of:

2-methylpyrazolo[1,5-b]-1,2,4-triazole,
2-ethylpyrazolo[1,5-b]-1,2,4-triazole,
2-isopropylpyrazolo[1,5-b]-1,2,4-triazole,
2-phenylpyrazolo[1,5-b]-1,2,4-triazole,
2,6-dimethylpyrazolo[1,5-b]-1,2,4-triazole,
6-methyl-2-ethylpyrazolo[1,5-b]-1,2,4-triazole,
6-methyl-2-isopropylpyrazolo[1,5-b]-1,2,4-triazole,
6-methyl-2-phenylpyrazolo[1,5-b]-1,2,4-triazole,
6-carboxy-2-methylpyrazolo[1,5-b]-1,2,4-triazole,
6-carboxy-2-ethylpyrazolo[1,5-b]-1,2,4-triazole,
6-carboxy-2-isopropylpyrazolo[1,5-b]-1,2,4-triazole,
6-carboxy-2-phenylpyrazolo[1,5-b]-1,2,4-triazole,
6-phenyl-2-methylpyrazolo[1,5-b]-1,2,4-triazole,
6-phenyl-2-ethylpyrazolo[1,5-b]-1,2,4-triazole,
6-phenyl-2-isopropylpyrazolo[1,5-b]-1,2,4-triazole,
6-phenyl-2-phenylpyrazolo[1,5-b]-1,2,4-triazole,
6-amino-2-methylpyrazolo[1,5-b]-1,2,4-triazole,
6-amino-2-ethylpyrazolo[1,5-b]-1,2,4-triazole,
6-amino-2-isopropylpyrazolo[1,5-b]-1,2,4-triazole,
6-amino-2-phenylpyrazolo[1,5-b]-1,2,4-triazole,
6-ethylthio-2-methylpyrazolo[1,5-b]-1,2,4-triazole,
6-ethylthio-2-ethylpyrazolo[1,5-b]-1,2,4-triazole,
6-ethylthio-2-isopropylpyrazolo[1,5-b]-1,2,4-triazole,
6-ethylthio-2-phenylpyrazolo[1,5-b]-1,2,4-triazole,
6-ethoxy-2-methylpyrazolo[1,5-b]-1,2,4-triazole,
6-ethoxy-2-ethylpyrazolo[1,5-b]-1,2,4-triazole,
6-ethoxy-2-isopropylpyrazolo[1,5-b]-1,2,4-triazole,
6-ethoxy-2-phenylpyrazolo[1,5-b]-1,2,4-triazole,
6-methyl-2-(2'-aminoethyl)pyrazolo[1,5-b]-1,2,4-triazole,
6-carboxy-2-(2'-aminoethyl)pyrazolo[1,5-b]-1,2,4-triazole,
6-phenyl-2-(2'-aminoethyl)pyrazolo[1,5-b]-1,2,4-triazole,
6-ethylthio-2-(2'-aminoethyl)pyrazolo[1,5-b]-1,2,4-triazole, 2-(2'-aminoethyl)pyrazolo[1,5-b]-1,2,4-triazole,
2-(2'-hydroxyethyl)pyrazolo[1,5-b]-1,2,4-triazole,
6-methyl-2-(2'-hydroxyethyl)pyrazolo[1,5-b]-1,2,4-triazole,
6-ethylthio-2-(2'-hydroxyethyl)pyrazolo[1,5-b]-1,2,4-triazole,
6-carboxy-2-(2'-hydroxyethyl)pyrazolo[1,5-b]- 1,2,4-triazole,
6-phenyl-2-(2'-hydroxyethyl)pyrazolo[1,5-b]-1,2,4-triazole,
7-chloro-2,6-dimethylpyrazolo[1,5-b]-1,2,4-triazole,
7-bromo-2,6-dimethylpyrazolo[1,5-b]-1,2,4-triazole, and their addition salts with an acid.

Among the compounds of formula (Ib) above very particular mention may be made of:
3-methylpyrazolo[3,2-c]-1,2,4-triazole,
3-methylsulphinyl-6-phenylpyrazolo[3,2-c]-1,2,4-triazole,
3-ethylpyrazolo[3,2-c]-1,2,4-triazole,
3-isopropylpyrazolo[3,2-c]-1,2,4-triazole,
3-phenylpyrazolo[3,2-c]-1,2,4-triazole,
3-(2'-aminoethyl)pyrazolo[3,2-c]-1,2,4-triazole,
3-(2'-hydroxyethyl)pyrazolo[3,2-c]-1,2,4-triazole,
6-methyl-3-ethylpyrazolo[3,2-c]-1,2,4-triazole,
3,6-dimethylpyrazolo[3,2-c]-1,2,4-triazole,
6-methyl-3-isopropylpyrazolo[3,2-c]-1,2,4-triazole,
6-methyl-3-phenylpyrazolo[3,2-c]-1,2,4-triazole,
6-methyl-3-(2'-aminoethyl)pyrazolo[3,2-c]-1,2,4-triazole,
6-methyl-3-(2'-hydroxyethyl)pyrazolo[3,2-c]-1,2,4-triazole,
6-methyl-3-methylthiopyrazolo[3,2-c]-1,2,4-triazole,
6-phenyl-3-methylpyrazolo[3,2-c]-1,2,4-triazole,
6-phenyl-3-ethylpyrazolo[3,2-c]-1,2,4-triazole,
6-phenyl-3-isopropylpyrazolo[3,2-c]-1,2,4-triazole,
6-phenyl-3-phenylpyrazolo[3,2-c]-1,2,4-triazole,
6-phenyl-3-(2'-aminoethyl)pyrazolo[3,2-c]-1,2,4-triazole,
6-phenyl-3-(2'-hydroxyethyl)pyrazolo[3,2-c]-1,2,4-triazole,
6-phenyl-3-methylthiopyrazolo[3,2-c]-1,2,4-triazole,
6-ethylthio-3-methylpyrazolo[3,2-c]-1,2,4-triazole,
6-ethylthio-3-ethylpyrazolo[3,2-c]-1,2,4-triazole,
6-ethylthio-3-isopropylpyrazolo[3,2-c]-1,2,4-triazole,
6-ethylthio-3-phenylpyrazolo[3,2-c]-1,2,4-triazole,
6-ethylthio-3-(2'-aminoethyl)pyrazolo[3,2-c]-1,2,4-triazole,
6-ethylthio-3-(2'-hydroxyethyl)pyrazolo[3,2-c]-1,2,4-triazole,
6-trifluoromethyl-3-methylthiopyrazolo[3,2-c]-1,2,4-triazole,
6-trifluoromethylpyrazolo[3,2-c]-1,2,4-triazole,
6-carboxy-3-methylpyrazolo[3,2-c]-1,2,4-triazole,
6-carboxy-3-ethylpyrazolo[3,2-c]-1,2,4-triazole,
6-carboxy-3-isopropylpyrazolo[3,2-c]-1,2,4-triazole,
6-carboxy-3-phenylpyrazolo[3,2-c]-1,2,4-triazole,
6-carboxy-3-(2'-aminoethyl)pyrazolo[3,2-c]-1,2,4-triazole,
6-carboxy-3-(2'-hydroxyethyl)pyrazolo[3,2-c]-1,2,4-triazole,
7-chloro-3,6-dimethylpyrazolo[3,2-c]-1,2,4-triazole,
7-methoxycarbonyl-3,6-dimethylpyrazolo[3,2-c]-1,2,4-triazole, and their addition salts with an acid.

As examples of compounds of formula (Ic) particular mention may be made of those fog which:
$R_1$ is hydrogen, methyl, trifluoromethyl, carboxyl, phenyl, ethoxy or cyano; and
$R_2$ is hydrogen or chlorine.

Among the compounds of formula (Ic) above very particular mention may be made of:
pyrazolo[5,1-e]tetrazole,
6-methylpyrazolo[5,1-e]tetrazole,
6-phenylpyrazolo[5,1-e]tetrazole,
6-carboxypyrazolo[5,1-e]tetrazole,
7-chloro-6-methylpyrazolo[5,1-e]tetrazole, and their addition salts with an acid.

As examples of compounds of formula (Id), particular mention may be made of those for which:
$R_1$ is hydrogen, methyl, trifluoromethyl, amino, carboxyl, phenyl, ethoxy or cyano;
$R_2$ is hydrogen or chlorine; and
$R_3$ and $R_4$ are respectively hydrogen and hydrogen, hydrogen and methyl, methyl and hydrogen, hydrogen and amino, or hydrogen and phenyl; or $R_3$ and $R_4$ together form a phenyl ring.

Among the compounds of formula (Id) above very particular mention may be made of:
pyrazolo[1,5-a]imidazole,
2-methylpyrazolo[1,5-a]imidazole,
2-phenylpyrazolo[1,5-a]imidazole,
pyrazolo[1,5-a]benzimidazole,
6-methylpyrazolo[1,5-a]imidazole,
2,6-dimethylpyrazolo[1,5-a]imidazole,
6-methyl-2-phenylpyrazolo[1,5-a]imidazole,
6-methylpyrazolo[1,5-a]benzimidazole,
6-phenylpyrazolo[1,5-a]imidazole,
6-phenyl-2-methylpyrazolo[1,5-a]imidazole,
2,6-diphenylpyrazolo[1,5-a]imidazole,
6-phenylpyrazolo[1,5-a]benzimidazole,
6-carboxypyrazolo[1,5-a]imidazole,
6-carboxy-2-methylpyrazolo[1,5-a]imidazole,
6-carboxy-2-phenylpyrazolo[1,5-a]imidazole,
6-carboxypyrazolo[1,5-a]benzimidazole,
6-ethoxypyrazolo[1,5-a]imidazole,
6-ethoxy-2-methylpyrazolo[1,5-a]imidazole,
6-ethoxy-2-phenylpyrazolo[1,5-a]imidazole,
6-trifluoromethylpyrazolo[1,5-a]benzimidazole,
6-aminopyrazolo[1,5-a]imidazole,
6-amino-2-methylpyrazolo[1,5-a]imidazole,
6-amino-2-phenylpyrazolo[1,5-a]imidazole,
6-aminopyrazolo[1,5-a]benzimidazole,
6-ethylthiopyrazolo[1,5-a]imidazole,
6-ethylthio-2-methylpyrazolo[1,5-a]imidazole,
6-ethylthio-2-phenylpyrazolo[1,5-a]imidazole,
7-chloro-6-methylpyrazolo[1,5-a]imidazole,
7-chloro-6-methylpyrazolo[1,5-a]benzimidazole, and their addition salts with an acid.

As examples of compounds of formula (Ie) particular mention may be made of those for which:

$R_1$ is hydrogen, methyl, trifluoromethyl, carboxyl, phenyl, ethoxy or cyano;

$R_2$ is hydrogen or chlorine; and $R_3$ and $R_4$ are respectively hydrogen and methyl, methyl and hydrogen, methyl and methyl or hydrogen and phenyl.

Among the compounds of formula (Ie) above very particular mention may be made of:

8-amino-4-methylpyrazolo[5,1-e]pyrazole, 8-amino-5-chloro-4-methylpyrazolo[5,1-e]pyrazole, and their addition salts with an acid.

As examples of compounds of formula (If) particular mention may be made of those for which:

$R_1$ is hydrogen, methyl, trifluoromethyl, carboxyl, phenyl, ethoxy or cyano;

$R_2$ is hydrogen or chlorine; and $R_3$ is hydrogen or methyl.

Among the compounds of formula (If) above very particular mention may be made of:

5-methylpyrazolo[5,1-e]-1,2,3-triazole, 5-methyl-6-chloropyrazolo[5,1-e]-1,2,3-triazole, 5-phenylpyrazolo[5,1-e]-1,2,3-triazole, and their addition salts with an acid.

A very particularly preferred compound of formula (I) is that of the following formula (Ia):

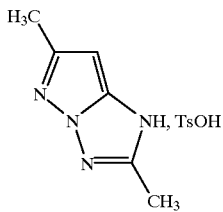

The compounds of the present invention, their synthesis intermediates and the processes for their preparation are described in the following patents and patent applications: FR 2 075 583, EP-A-119 860, EP-A-285 274, EP-A-244 160, EP-A-578 248, GB 1 458 377, U.S. Pat. No. 3,227,554, U.S. Pat. No. 3,419,391, U.S. Pat. No. 3,061,432, U.S. Pat. No. 4,500,630, U.S. Pat. No. 3,725,067, U.S. Pat. No. 3,926,631, U.S. Pat. No. 5,457,210, JP 84/99437, JP 83/42045, JP 84/162548, JP 84/171956, JP 85/33552, JP 85/43659, JP 85/172982, JP 85/190779, and also in the following publications: Chem. Ber. 32, 797 (1899), Chem. Ber 89, 2550, (1956), J. Chem. Soc. Pekin trans. I, 2047, (1977), J Prakt. Chem., 320, 533, (1978) , J. für Chem., 32(5) , 829, (1984).

The compound or compounds of formula (I) represent preferably from 0.0005 to 12% by weight, approximately, of the total weight of the dyeing composition and more preferably from 0.005 to 6% by weight, approximately, of this weight.

The nature of the oxidation base or bases which can be employed in the dyeing composition according to the invention is not critical. This or these oxidation base or bases are preferably selected from para-phenylenediamines, bis-phenylalkylenediamines, para-aminophenols, ortho-aminophenols, heterocyclic bases, and their addition salts with an acid.

Among the para-phenylenediamines which can be used as oxidation bases in the dyeing composition according to the invention particular mention may be made of the compounds of the following formula (II) and their addition salts with an acid:

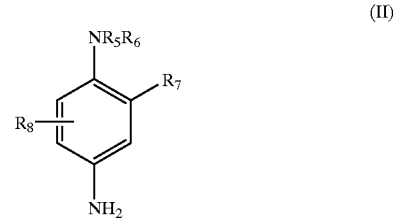

in which:

$R_5$ is a hydrogen atom or a $C_1$–$C_4$ alkyl, $C_1$–$C_4$ monohydroxyalkyl, $C_2$–$C_4$ polyhydroxyalkyl or $C_2$–$C_4$-alkoxy-$C_1$–$C_4$-alkyl radical, $R_6$ is a hydrogen atom or a $C_1$–$C_4$ alkyl, $C_1$–$C_4$ monohydroxyalkyl or $C_2$–$C_4$ polyhydroxyalkyl radical, $R_7$ is a hydrogen atom, a halogen atom, such as a chlorine atom, or a $C_1$–$C_4$ alkyl, sulpho, carboxyl, $C_1$–$C_4$ monohydroxyalkyl or $C_1$–$C_4$ hydroxyalkoxy radical, and $R_8$ is a hydrogen atom or a $C_1$–$C_4$ alkyl radical.

In the formula (II) above and when $R_7$ is other than a hydrogen atom, $R_5$ and $R_6$ are preferably a hydrogen atom and $R_7$ is preferably identical to $R_8$ and, when $R_7$ is a halogen atom, $R_5$, $R_6$ and $R_9$ are preferably a hydrogen atom.

Among the para-phenylenediamines of formula (II) above more particular mention may be made of para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis-(β-hydroxyethyl)-para-phenylenediamine, 4-amino-1-(β-methoxyethyl) aminobenzene and 2-chloro-para-phenylenediamine, and their addition salts with an acid.

Among the bis-phenylalkylenediamines which can be used as oxidation bases in the dyeing composition according to the invention particular mention may be made of the compounds of the following formula (III) and their addition salts with an acid:

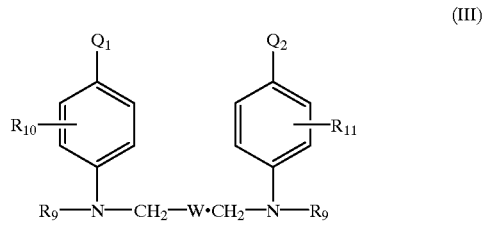

in which:

$Q_1$ and $Q_2$ are identical or different and are a hydroxyl radical or a radical $NHR_{12}$ in which $R_{12}$ is a hydrogen atom or a $C_1$–$C_4$ alkyl radical, $R_9$ is a hydrogen atom or a $C_1$–$C_4$ alkyl, $C_1$–$C_4$ monohydroxyalkyl or $C_2$–$C_4$ polyhydroxyalkyl radical or a $C_1$–$C_4$ aminoalkyl radical in which the amino moiety may be substituted, $R_{10}$ and $R_{11}$, are identical or different and are a hydrogen or halogen atom or a $C_1$–$C_4$ alkyl radical, and W is a radical taken from the group consisting of the following radicals:

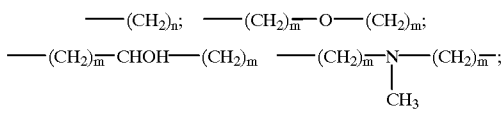

in which n is an integer from 0 to 8 inclusive and m is an integer from 0 to 4 inclusive.

Among the bis-phenylalkylenediamines of formula (III) above more particular mention may be made of N,N'-bis(β-hydroxyethyl)-N,N'-bis(4'-aminophenyl)-1,3-diamino-2-propanol, N,N'-bis(β-hydroxyethyl)-N,N'-bis(4'-aminophenyl)ethylenediamine, N,N'-bis(4'-aminophenyl)tetramethylenediamine, N,N'-bis(β-hydroxyethyl)-N,N'-bis(4-aminophenyl)tetramethylene-diamine, N,N'-bis(4-methylaminophenyl)tetramethylene-diamine and N,N'-bis(ethyl)-N,N'-bis(4'-amino-3'-methylphenyl)ethylenediamine and their addition salts with an acid.

Among these bis-phenylalkylenediamines of formula (III), N,N'-bis(β-hydroxyethyl)-N,N'-bis(4'-aminophenyl)-1,3-diaminopropanol or one of its addition salts with an acid is particularly preferred.

Among the para-aminophenols which can be used as oxidation bases in the dyeing composition according to the invention particular mention may be made of the compounds of the following formula (IV) and their addition salts with an acid:

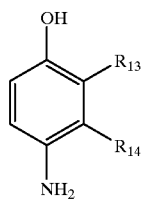

(IV)

in which:
R$_{13}$ is a hydrogen atom or a C$_1$–C$_4$ alkyl, C$_1$–C$_4$ monohydroxyalkyl, C$_1$–C$_4$-alkoxy-C$_1$–C$_4$-alkyl or C$_1$–C$_4$ aminoalkyl radical, R$_{14}$ is a hydrogen or fluorine atom or a C$_1$–C$_4$ alkyl, C$_1$–C$_4$ monohydroxyalkyl, C$_2$–C$_4$ polyhydroxyalkyl, C$_1$–C$_4$ aminoalkyl, C$_1$–C$_4$ cyanoalkyl or C$_1$–C$_4$-alkoxy-C$_1$–C$_4$-alkyl radical, it being understood that at least one of the radicals R$_{13}$ and R$_{14}$ is a hydrogen atom.

Among the para-aminophenols of formula (IV) above more particular mention may be made of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxyethylaminomethyl)phenol and their addition salts with an acid.

Among the ortho-aminophenols which can be used as oxidation bases in the dyeing composition according to the invention particular mention may be made of 2-aminophenol, 2-amino-1-hydroxy-5-methylbenzene, 2-amino-1-hydroxy-6-methylbenzene and 5-acetamido-2-aminophenol and their addition salts with an acid.

Among the heterocyclic bases which can be used as oxidation bases in the dyeing composition according to the invention particular mention may be made of pyridine derivatives, pyrimidine derivatives, and pyrazole derivatives and their addition salts with an acid.

Among the pyridine derivatives more particular mention may be made of the compounds described, for example, in the patents GB 1 026 978 and GB 1 153 196, such as 2,5-diaminopyridine, and their addition salts with an acid.

Among the pyrimidine derivatives more particular mention may be made of the compounds described, for example, in the German patent DE 2359399 or Japanese patents JP 88-169 571 and JP 91-333 495, such as 2,4,5,6-tetraaminopyrimidine and 4-hydroxy-2,5,6-triaminopyrimidine, and their addition salts with an acid.

Among the pyrazole derivatives more particular mention may be made of the compounds described in the patents DE 3843892 and DE 4133957 and patent applications WO 94/08969 and WO 94/08970, such as 4,5-diamino-1-methylpyrazole, 3,4-diaminopyrazole and 1-(4'-chlorobenzyl)-4,5-diaminopyrazole, and their addition salts with an acid.

According to the invention, the oxidation base or bases represent preferably from 0.0005 to 12% by weight, approximately, of the total weight of the dyeing composition, and more preferably from 0.005 to 6% by weight, approximately, of this weight.

The dyeing composition according to the invention may also comprise one or more additional couplers other than the compounds of formula (I) and/or one or more direct dyes, so as to vary, or enrich with glints, the shades obtained with the oxidation bases.

The additional couplers which can be used in the composition according to the invention can be selected from the couplers used conventionally in oxidation dyeing, among which mention may be made, in particular, of meta-phenylenediamines, meta-aminophenols, meta-diphenols and heterocyclic couplers such as, for example, indole derivatives and indoline derivatives, and their addition salts with an acid.

These couplers can in particular be selected from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethyl-amino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole and 6-hydroxyindoline, and their addition salts with an acid.

When present, these additional couplers represent preferably from 0.0005 to 5% by weight, approximately, of the total weight of the dyeing composition, and more preferably from 0.005 to 3% by weight, approximately, of this weight.

The addition salts with an acid of the oxidation base or bases and/or of the additional couplers which can be used in the dyeing composition of the invention are selected in particular from hydrochlorides, hydrobromides, sulphates and tartrates, and lactates and acetates.

The medium appropriate for dyeing (or vehicle) generally consists of water or of a mixture of water and at least one organic solvent, in order to solubilize the compounds which would not be sufficiently soluble in water As organic solvent mention may be made, for example, of lower C$_1$–C$_4$ alcohols, such as ethanol and isopropanol; glycerol; glycols and glycol ethers, such as 2-butoxyethanol, propylene glycol, propylene glycol monomethyl ether, diethylene glycol monoethyl and monomethyl ether, and aromatic alcohols, such as benzyl alcohol or phenoxyethanol, similar products, and mixtures thereof.

The solvents may be present in proportions preferably of between approximately 1 and 40% by weight relative to the total weight of the dyeing composition and, more preferably, between approximately 5 and 30% by weight.

The pH of the dyeing composition in accordance with the invention is generally between 3 and 12. It can be adjusted to the desired value by means of acidifying or basifying agents commonly used in the dyeing of keratinous fibres.

Among the acidifying agents, mention may be made by way of example of mineral acids or organic acids, such as hydrochloric acid, orthophosphoric acid, carboxylic acids such as tartaric acid, citric acid and lactic acid, and sulphonic acids.

Among the basifying agents mention may be made, by way of example, of aqueous ammonia, alkali metal carbonates, alkanolamines, such as mono-, di- and triethanolamines, and derivatives thereof, sodium hydroxide or potassium hydroxide, and the compounds of the following formula (V):

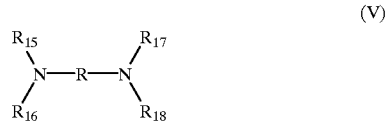

in which R is a propylene radical optionally substituted by a hydroxyl group or a $C_1$–$C_4$ alkyl radical; and $R_{15}$, $R_{16}$, $R_{17}$ and $R_{18}$ are identical or different and are a hydrogen atom or a $C_1$–$C_4$ alkyl or $C_1$–$C_4$ hydroxyalkyl radical The dyeing composition according to the invention may also comprise various adjuvants used conventionally in hair dyeing compositions, such as anionic, cationic, nonionic, amphoteric or zwitterionic surfactants or mixtures thereof, anionic, cationic, nonionic, amphoteric or zwitterionic polymers or mixtures thereof, organic or inorganic thickeners, antioxidants, penetration agents, sequestering agents, fragrances, buffers, dispersants, conditioners such as, for example, silicones, film formers, preservatives and opacifiers.

The person skilled in the art will of course take care to select the optional complementary compounds mentioned above such that the advantageous properties intrinsic to the dyeing composition according to the invention are not, or not substantially, impaired by the intended addition or additions.

The dyeing composition according to the invention may be in various forms, such as in the form of liquids, creams, gels or any other form which is appropriate for dyeing keratinous fibres and especially human hair.

The invention also provides for the use of the pyrazoloazoles of formula (I) above, as couplers, in combination with at least one oxidation base for the oxidation dyeing of keratinous fibres, and especially human keratinous fibres such as hair.

The invention also provides a method of oxidation-dyeing keratinous fibres, and especially human keratinous fibres such as hair, which employs the dyeing composition as defined above.

According to this method, at least one dyeing composition as defined above is applied to the fibres, the colour being developed at acidic, neutral or alkaline DH with the aid of an oxidizing agent which is added right at the time when the dyeing composition is employed or which is present in an oxidizing composition which is applied simultaneously or sequentially and separately.

According to a particularly preferred embodiment of the dyeing method according to the invention, the above-described dyeing composition is mixed at the time of use with an oxidizing composition comprising, in a medium appropriate for dyeing, at least one oxidizing agent which is present in an amount sufficient to develop a coloration. The mixture obtained is then applied to the keratinous fibres and left to act for approximately 3 to 50 minutes, preferably for approximately 5 to 30 minutes, after which the fibres are rinsed, shampooed, rinsed again and dried.

The oxidizing agent present in the oxidizing composition as defined above can be selected from the oxidizing agents conventionally used for the oxidation dyeing of keratinous fibres, among which mention may be made of hydrogen peroxide, urea peroxide, alkali metal bromates, and persalts, such as perborates and persulphates. Hydrogen peroxide is particularly preferred.

The pH of the oxidizing composition comprising the oxidizing agent as defined above is such that, after it has been mixed with the dyeing composition, the pH of the resulting composition applied to the keratinous fibres varies preferably between approximately 3 and 12 and, still more preferably, between 5 and 11. It is adjusted to the desired value by means of acidifying or basifying agents commonly employed in the dyeing of keratinous fibres and as defined above.

The oxidizing composition as defined above may also comprise various adjuvants conventionally employed in hair dyeing compositions and as defined above.

The composition which is ultimately applied to the keratinous fibres may be in various forms, such as in the form of liquids, creams or gels or in any other form appropriate for dyeing keratinous fibres and especially human hair.

The invention additionally provides a multi-compartment dyeing device or kit or any other multi-compartment packaging system, a first compartment of which contains the dyeing composition as defined above and a second compartment of which contains the oxidizing composition as defined above.

These devices may be equipped with a means which allows the desired mixture to be delivered to the hair, such as the devices described in the patent FR-2 586 913 in the name of the Applicant.

The examples which follow serve to illustrate the invention without, however, being limitative in nature.

EXAMPLES

Preparation Example A

The synthesis of 1H-2,6-dimethylpyrazolo[1,5-b]-1,2,4-triazole tosylate of structure:

compound D

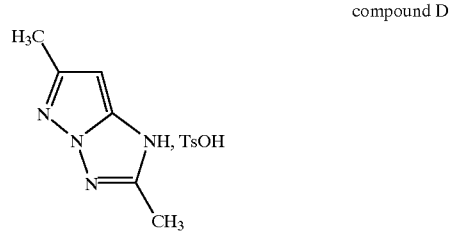

-continued
SYNTHESIS SCHEME

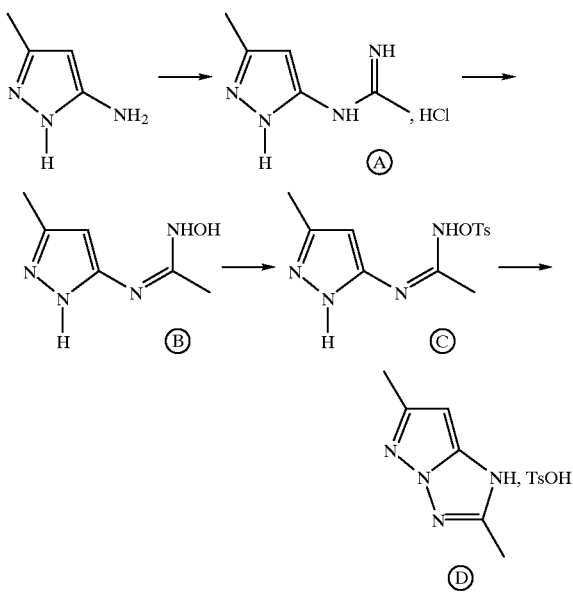

15.7 g (0.16 mol) of 5-amino-3-methylpyrazole were added in small portions and with stirring to a solution of 20 g (0.16 mol) of ethyl acetimidate hydrochloride in 100 cm³ of anhydrous ethanol, while maintaining the temperature below 30° C. Stirring was maintained for 1 hour more. The reaction medium was subsequently concentrated to 45° C. under a vacuum of 60 mm of mercury until crystallization began. It was then cooled to room temperature and the precipitate was filtered over a glass frit and then dried under vacuum at a temperature of 45° C. This gave 16 g of compound A in the form of white crystals whose melting point was 249° C.

83.5 cm³ of a 4.8 M (0.4 mol) methanolic solution of sodium methylate was added slowly to a solution of 70 g (0.4 mol) of compound A, prepared as above, in 300 cm³ of anhydrous methanol. Sodium chloride formed, and was separated off by filtration. The filtrate was cooled to 0° C. and poured into a solution of hydroxylamine which was itself cooled at 0° C. and had been prepared beforehand from 33.4 g (0.48 mol) of hydroxylamine hydrochloride, 20 cm³ of anhydrous methanol and 100 cm³ of 4.8 M (0.48 mol) sodium methanolate solution, the sodium chloride formed having been separated off by filtration.

The reaction medium was subsequently heated at reflux with stirring for 24 hours and then cooled to approximately 0° C. A white solid crystallized out. It was filtered over a glass frit, washed with ice-cold methanol and dried under vacuum at 40° C. 26.4 g of compound B were weighed. The filtrate was concentrated under vacuum, and a second fraction of 7.6 g of compound B was isolated in the same way. The two fractions were combined to give 34.3 g of compound B in the form of a white solid whose melting point was 197° C.

20.05 cm³ (0.143 mol) of anhydrous triethylamine and then 27.2 g (0.143 mol) of the acid chloride of para-toluenesulphonic acid were added to a solution of 20 g (0.13 mol) of compound B, prepared as above, in 9.5 liters of anhydrous tetrahydrofuran. The reaction medium was stirred at ambient temperature for two hours and then cooled to 0° C. The triethylamine hydrochloride was separated off by filtration and the filtrate was concentrated under a vacuum of 60 mm of mercury at approximately 50° C. until crystallization began. It was then cooled to 0° C. and the precipitate was filtered over a glass frit, washed with ice-cold tetrahydrofuran and then dried under vacuum at a temperature of 40° C. This gave 36.2 g of compound C in the form of a white solid whose melting point was between 105° C. and 128° C. (decomposition).

A solution of 35 g (0.113 mol) of compound C, obtained above, in 1 liter of methanol was heated at reflux for 2 hours and then evaporated to dryness. An oil was obtained which crystallized when 100 cm³ of isopropyl ether were added. The crystals were filtered over a glass frit and then recrystallized from a mixture of isopropanol and heptane. Drying under vacuum at 40° C. gave 19 g of 1H-2,6-dimethylpyrazolo[1,5-b]-1,2,4-triazole tosylate (compound D) in the form of a white solid whose melting point was 157° C.

Elemental analysis for $C_6H_9N_4$, $C_7H_7O_3S$:

|  | C | H | N | O | S |
|---|---|---|---|---|---|
| calculated | 50.64 | 5.23 | 18.17 | 15.57 | 10.40 |
| found | 50.54 | 5.37 | 18.27 | 16.12 | 10.40 |

EXAMPLES 1 TO 5—DYEING IN AN ALKALINE MEDIUM

The following dyeing compositions in accordance with the invention were prepared (contents in grams):

| Example | 1 | 2 | 3 | 4 | 5 |
|---|---|---|---|---|---|
| Compound of Preparation Example A (coupler) | 0.925 | 0.925 | 0.925 | 0.925 | 0.925 |
| Para-phenylenediamine (oxidation base) | 0.324 | — | — | — | — |
| Para-tolylenediamine sulphate (oxidation base) | — | 0.660 | — | — | 0.805 |
| N-Propyl-para-phenylenediamine, dihydrochloride salt (oxidation base) | — | — | 0.669 | — | — |
| Para-aminophenol (oxidation base) | — | — | — | 0.327 | — |
| 1-Methyl-3-methyl-diaminopyrazole dihydrochloride (oxidation base) | — | — | — | — | 0.597 |
| Common dye vehicle | No. 1 | No. 1 | No. 1 | No. 1 | No. 1 |
| Demineralized water q.s. | 100 g | 100 g | 100 g | 100 g | 100 g |

| Common dye vehicle No. 1: | |
|---|---|
| Oleyl alcohol polyglycerolated with 2 mol of glycerol | 4.0 g |
| Oleyl alcohol polyglycerolated with 4 mol of glycerol, containing 78% active substance (a.s.) | 5.69 g a.s. |
| Oleic cid | 3.0 g |
| Oleylamine containing 2 mol of ethylene oxide, sold under the tradename ETHOMEEN 012 by the company AKZO | 7.0 g |
| Diethylaminopropyl laurylaminosuccinamate, sodium salt, containing 55% of a.s. | 3.0 g a.s. |

-continued

| Common dye vehicle No. 1: | |
|---|---|
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Aqueous sodium metabisulphite solution containing 35% of a.s. | 0.455 g a.s. |
| Ammonium acetate | 0.8 g |
| Antioxidant, sequestering agent | q.s. |
| Fragrance, preservative | q.s. |
| Aqueous ammonia containing 20% $NH_3$ | 10.0 g |

Each dyeing compositions of Examples 1 to 5 was mixed at the time of use with an equal weight of 20-volumes hydrogen peroxide (6% by weight).

Each of the resulting mixtures was applied for 30 minutes to locks of natural grey hair containing 90% white hairs, with or without permanent-waving, in an amount of 28 g per 3 g of hair. After rinsing, washing with a standard shampoo and drying, the locks were dyed in the shades indicated in Table 1 below.

The colour of the locks was evaluated in the MUNSELL system using a MINOLTA CM 2002 calorimeter.

In the MUNSELL notation a colour is defined by the expression H V/C, where the three parameters denote, respectively, the shade or hue (H), the intensity or value (V) and the purity or chromaticity (C), the oblique bar in this expression being simply a convention and not indicating a ratio.

The results are given in Table 1 below:

TABLE 1

| Example | Shade obtained on natural grey hair containing 90% white hairs | Shade obtained on permanent-waved grey hair containing 90% white hairs |
|---|---|---|
| 1 | Iridescent dark purple 8.5 RP 3.0/4.2 | Intense iridescent dark purple 10.5 RP 2.6/4.0 |
| 2 | Iridescent 8.1 RP 3.4/5.3 | Intense iridescent 8.8 RP 3.2/5.7 |
| 3 | Iridescent 8.2 RP 3.7/5.6 | Intense iridescent 9.3 RP 3.1/5.9 |
| 4 | Iridescent, slightly coppery 0.2 YR 4.7/2.9 | Iridescent copper 0.7 YR 4.6/3.0 |
| 5 | Coppery natural gold 9.5 YR 5.3/3.4 | Coppery gold 8.9 YR 4.9/3.8 |

EXAMPLES 6 TO 9—DYEING IN AN ALKALINE MEDIUM

The following dyeing compositions in accordance with the invention were prepared (contents in grams):

| Examples | 6 | 7 | 8 | 9 |
|---|---|---|---|---|
| 3,6-Dimethylpyrazolo[3,2-c]-1,2,4-triazole (coupler) | 0.408 | 0.408 | 0.408 | — |

-continued

| Examples | 6 | 7 | 8 | 9 |
|---|---|---|---|---|
| 6-Phenyl-3-methylthio-pyrazolo[3,2-c]-1,2,4-triazole (coupler) | — | — | — | 0.691 |
| Para-tolylenediamine (oxidation base) | 0.366 | — | — | 0.366 |
| Para-aminophenol (oxidation base) | — | 0.327 | — | — |
| 3,7-Diaminopyrazolopyrimidine dihydrochloride (oxidation base) | — | — | 0.666 | — |
| Common dye vehicle | No. 2 | No. 2 | No. 2 | No. 2 |
| Demineralized water q.s. | 100 g | 100 g | 100 g | 100 g |

NB: 3,6-Dimethylpyrazolo[3,2-c]-1,2,4-triazole and 6-phenyl-3-methylthiopyrazolo[3,2-c]-1,2,4-triazole were prepared by the process described in J. Chem. Soc. Perkin trans. I, 2047 (1977).

| Common dye vehicle No. 2: | |
|---|---|
| Ethanol | 20 g |
| Aqueous ammonia containing 20% $NH_3$ | 10 g |
| Sodium metabisulphite | 0.228 g |
| Sequestering agent | q.s. |

Each of the dyeing compositions from Examples 6 to 9 above was mixed at the time of use with an equal weight of 20-volumes hydrogen peroxide solution (6% by weight).

Each of the resulting mixtures was applied for 30 minutes to locks of natural grey hair containing 90% white hairs, with or without permanent-waving, in an amount of 10 g per 1 g of hair. After rinsing, washing with a standard shampoo and drying, the locks were dyed in the shades indicated in Table 2 below:

TABLE 2

| Example | pH of the mixture | Shade obtained on natural grey hair containing 90% white hairs | Shade obtained on permanent-waved grey hair containing 90% white hairs |
|---|---|---|---|
| 6 | 10.0 | Iridescent red | Iridescent red |
| 7 | 10.1 | Iridescent copper | Iridescent copper |
| 8 | 9.8 | Golden copper | Copper |
| 9 | 10.2 | Dark purple | Dark purple |

EXAMPLES 10 AND 11—DYEING IN AN ALKALINE MEDIUM

The following dyeing compositions in accordance with the invention were prepared (contents in grams):

| Examples | 10 | 11 |
|---|---|---|
| 6-Methylpyrazolo[1,5-a]benzimidazole (coupler) | 0.514 | — |
| 7-Chloro-2,6-dimethylpyrazolo[1,5-b]-1,2,4-triazole (coupler) | — | 0.512 |
| Para-phenylenediamine (oxidation base) | 0.324 | 0.324 |
| Common dye vehicle | No. 3 | No. 3 |
| Demineralized water q.s. | 100 g | 100 g |

NB: 6-Methylpyrazolo[1,5-a]benzimidazole was prepared by the process described in J. für Chem., 326(5), 829 (1984)

and 7-chloro-2,6-dimethylpyrazolo[1,5-b]-1,2,4-triazole was prepared by the process described in the Patent Application EP-A-119 860.

| Common dye vehicle No. 3: | |
|---|---|
| Benzyl alcohol | 2.0 g |
| Polyethylene glycol containing 6 mol of ethylene oxide | 3.0 g |
| Ethanol | 20.0 g |
| $C_8$—$C_{10}$-Alkyl polyglucoside in aqueous solution containing 60% of active substance, buffered with ammonium citrate, sold under the name ORAMIX CG110 by the company SEPPIC | 6.0 g |
| Aqueous ammonia containing 20% $NH_3$ | 10.0 g |
| Sodium metabisulphite | 0.228 g |
| Sequestering agent | q.s. |

Each of the dyeing compositions of Examples 10 and 11 above was mixed at the time of use with an equal weight of 20-volumes hydrogen peroxide solution (6% by weight). Each of the resulting mixtures was applied for 30 minutes to locks of natural grey hair containing 90% white hairs, with or without permanent-waving, in an amount of 10 g per 1 g of hair. After rinsing, washing with a standard shampoo and drying, the locks were dyed in the, shades indicated in Table 3 below:

TABLE 3

| Example | pH of the mixture | Shade obtained on natural grey hair containing 90% white hairs | Shade obtained on permanent-waved grey hair containing 90% white hairs |
|---|---|---|---|
| 10 | 10.1 | Subdued iridescent | Slightly dark purple iridescent |
| 11 | 10.1 | Iridescent | Slightly red iridescent |

EXAMPLE 12—DYEING IN AN ALKALINE MEDIUM

The same dyeing composition as that used for Example 10 above was prepared. This dyeing composition was mixed at the time of use with an equal quantity by weight of a $6\times10^{-3}$ mol-% aqueous ammonium persulphate solution. The resulting mixture had a pH of 9.9 and was applied for 30 minutes to locks of natural grey hair containing 90% white hairs, with or without permanent-waving, in an amount of 10 g per 1 g of hair. After rinsing, washing with a standard shampoo and drying, the locks were dyed in an iridescent golden shade on natural hair and in a slightly red iridescent shade on permed hair.

EXAMPLES 13 to 17—DYEING IN A NEUTRAL MEDIUM

The following dyeing compositions in accordance with the invention were prepared (contents in grams):

| Examples | 13 | 14 | 15 | 16 | 17 |
|---|---|---|---|---|---|
| 3,6-Dimethylpyrazolo[3,2-c]-1,2,4-triazole (coupler) | 0.408 | 0.408 | — | — | — |
| 6-Phenyl-3-methyl-thiopyrazolo[3,2-c]-1,2,4-triazole (coupler) | — | — | 0.691 | — | — |
| 7-Chloro-2,6-dimethylpyrazolo[1,5-b]-1,2,4-triazole (coupler) | — | — | — | 0.512 | — |
| 6-Methyl-pyrazolo[5,1-e]tetrazole (coupler) | — | — | — | — | 0.370 |
| para-tolylenediamine (oxidation base) | 0.366 | — | — | — | — |
| 3,7-Diaminopyrozolo-pyrimidine dihydrochloride (oxidation base) | — | 0.666 | 0.666 | — | — |
| Para-phenylenediamine (oxidation base) | — | — | — | 0.324 | — |
| 4-(2-Methoxyethyl-amino) aniline dihydrochloride (oxidation base) | — | — | — | — | 0.717 |
| Common dye vehicle | No. 4 | No. 4 | No. 4 | No. 5 | No. 4 |
| Demineralized water q.s. | 100 g | 100 g | 100 g | 100 g | 100 g |

NB: 6-methylpyrazolo[5,1-e]tetrazole was prepared by the process described in the patent JP 60 33 552.

| Common dye vehicle No. 4: | |
|---|---|
| Ethanol | 20.0 g |
| $K_2HPO_4/KH_2PO_4$ (1.5M/1M) buffer | 10.0 g |
| Sodium metabisulphite | 0.228 g |
| Sequestering agent | q.s |

| Common dye vehicle No. 5: | |
|---|---|
| Benzyl alcohol | 2.0 g |
| Polyethylene glycol 6 EO | 3.0 g |
| Ethanol | 20.0 g |
| $C_8$—$C_{10}$-Alkyl polyglucoside in aqueous solution containing 60% active substance, buffered with ammonium citrate, sold under the name ORAMIX CG 110 by the company SEPPIC | 6.0 g |
| $K_2HPO_4/KH_2PO_4$ (1.5M/1M) buffer | 10.0 g |
| Sodium metabisulphite | 0.228 g |
| Sequestering agent | q.s |

Each of the dyeing compositions of Examples 13 to 17 above was mixed at the time of use with an equal weight of a 20-volume hydrogen peroxide solution (6% by weight).

Each of the mixtures obtained was applied for 30 minutes to locks of natural grey hair containing 90% white hairs, with or without permanent-waving, in an amount of 10 g per 1 g of hair. After rinsing, washing with a standard shampoo and drying, the locks were dyed in the shades indicated in Table 4 below:

TABLE 4

| Example | pH of the mixture | Shade obtained on natural grey hair containing 90% white hairs | Shade obtained on permanent-waved grey hair containing 90% white hairs |
|---|---|---|---|
| 13 | 7.1 | Iridescent red | Iridescent red |
| 14 | 6.9 | Subdued golden copper | Copper |
| 15 | 6.7 | Iridescent copper | Reddish copper |
| 16 | 6.8 | Dark purple | Deep dark purple |
| 17 | 6.8 | Mauvish blue-grey | Bluish grey |

What is claimed is:

1. A method of oxidation-dyeing keratin fibers, comprising:
   (a) applying to the fibers an effective amount for dyeing of at least one dyeing composition, and
   (b) developing color at acidic, neutral, or alkaline pH in the presence of an oxidizing agent which is added to the dyeing composition at the time that the dyeing composition is applied, or which is present in an oxidizing composition that is applied:
      (i) separately from the dyeing composition at the same time that the dyeing composition is applied to the fibers, or
      (ii) sequentially with the dyeing composition,
   wherein said dyeing composition comprises, in a medium which is suitable for dyeing:
      (a) a coupler, wherein said coupler is at least one pyrazolo-azole compound of the formula (I) or an acid addition salt thereof:

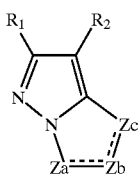

(I)

wherein:

$R_1$ is a hydrogen atom; a linear or branched $C_1$–$C_{20}$ alkyl radical, which is unsubstituted or substituted by one or two radicals R, wherein R is halogen, nitro, cyano, hydroxyl, alkoxy, aryloxy, amino, alkylamino, acylamino, carbamoyl, sulphonamido, sulphamoyl, imido, alkylthio, arylthio, aryl, alkoxycarbonyl, trifluoromethyl, or acyl; an aryl radical, which is unsubstituted or substituted by one or two radicals R as defined above; or a 5- or 6-membered heterocycle which has at least one nitrogen, oxygen, or sulphur atom, and is unsubstituted or substituted by one or two radicals R as defined above;

wherein if $R_1$ is an alkyl radical, an aryl radical or a 5- or 6-membered heterocycle as defined above, $R_1$ can also be attached to the carbon atom of the ring system by an oxygen, nitrogen, or sulphur atom, such that $R_1$ becomes $XR_1$ wherein X=O, NH, or S;

$R_1$ may also be a halogen atom; an acyl radical; a sulphonyl radical; a sulphinyl radical; a phosphonyl radical; a carbamoyl radical; a sulphamoyl radical; a cyano radical; a siloxy radical; an amino radical; an acylamino radical; an acyloxy radical; a carbamoyloxy radical; a sulphonamide radical; an imide radical; a ureido radical; a sulphamoylamino radical; an alkoxycarbonylamino radical; an aryloxycarbonylamino radical; an alkoxycarbonyl radical; an aryloxycarbonyl radical; a trifluromethyl radical; or a carboxyl radical;

$R_2$ is a hydrogen atom; a halogen atom; an acetylamido radical; an alkoxy radical; an aryloxy radical; an acyloxy radical; arylthio radical; an alkythio radical; a heteroarylthio radical; a heteroaryloxy radical; a thiocyano radical; an N,N-diethylthiocarbonylthio radical; a dodecyloxythiocarbonylthio radical; a benzenesulphonamido radical; an N-ethyltoluenesulphonamido radical; a pentafluorobutanamido radical; a 2,3,4,5,6-pentafluorobenzamido radical; a p-cyanophenylureido radical; an N,N-diethylsulphamoylamino radical, a pyrazolyl radical; an imidazolyl radical; a triazolyl radical; a tetrazolyl radical; a benzimidazolyl radical; a 1-benzyl-5-ethoxy-3-hydantoinyl radical; a 1-benzyl-3-hydantoinyl radical; 5,5-dimethyl-2,4-dioxo-3-oxazolidinyl; a 2-oxy-1,2-dihydro-1-pyridinyl radical; an alkylamido; an arylamido; a radical $NR'''R^{IV}$, wherein $R'''$ and $R^{IV}$ are each independently a $C_1$–$C_4$ alkyl or a hydroxyalkyl; a carboxyl; or an alkoxycarboxyl radical;

$Z_a$, $Z_b$ and $Z_c$ are each independently a nitrogen atom, a carbon atom carrying a radical $R_3$ or $R_4$, wherein $R_3$ and $R_4$ each independently have the same definition as radical $R_1$; with the proviso that at least one of the radicals $Z_a$, $Z_b$ and $Z_c$ is other than a carbon atom, find that $R_3$ and $R_4$ may also together form a substituted or unsubstituted aromatic ring; and (b) at least one oxidation base or an acid addition salt thereof.

2. A method according to claim 1, wherein the radical $R_1$ of the formula (I) is a hydrogen atom; a linear or branched $C_1$–$C_4$ alkyl; a phenyl; a phenyl substituted by a halogen atom, a $C_1$–$C_4$ alkyl, a $C_1$–$C_4$ alkoxy, a nitro group, an amino group, a trifluoromethyl group or $C_1$–$C_4$ alkylamino group; a benzyl radical; a benzyl radical substituted by a halogen atom, a $C_1$–$C_4$ alkyl, a $C_1$–$C_4$ alkoxy, a nitro group, an amino group or a trifluoromethyl group; a $C_1$–$C_4$ alkylamino; a heterocycle which is thiophene, furan or pyridine; a trifluoromethyl radical; a radical $(CH_2)_p$—X—$(CH_2)_q$—OR', where p and q are identical or different integers from 1 to 3, R' is H or methyl, and X is an oxygen atom or a group NR" where R" is hydrogen or methyl; a $C_1$–$C_4$ hydroxyalkyl; a $C_1$–$C_4$ aminoalkyl; a $C_1$–$C_4$ alkylamino; a $C_1$–$C_4$ dialkylamino; an arylamino; an alkoxy radical which is methoxy, ethoxy, or phenoxy; a halogen which is fluorine, chlorine or bromine; a carboxyl group; a $C_1$–$C_4$ alkoxycarbonyl; a phenyloxycarbonyl; methylthio; ethylthio; phenylthio; methanesulphonyl; or cyano.

3. A method according to claim 1, wherein the radical $R_1$ of the formula (I) is hydrogen; methyl; ethyl; isopropyl; tert-butyl; fluorine; chlorine; phenyl; tolyl; 4-chlorophenyl; 4-methoxyphenyl; 3-methoxyphenyl; 2-methoxyphenyl; benzyl; a heterocycle which is pyridyl, furyl or thienyl; trifluoromethyl; hydroxymethyl; aminomethyl; methoxy; ethoxy; methylamino; ethylamino; dimethylamino; carboxyl; methoxycarbonyl; ethoxycarbonyl; or cyano.

4. A method according to claim 3, wherein the radical $R_1$ of the formula (I) is hydrogen; methyl; ethyl; phenyl; tolyl; 4-chlorophenyl; 4-methoxyphenyl; benzyl; trifluoromethyl; chloro; methoxy; ethoxy; carboxyl; methylamino; dimethylamino; or cyano.

5. A method according to claim 1, wherein the radical $R_2$ of the formula (I) is a hydrogen atom; a $C_1$–$C_4$ alkoxy; phenoxy; phenoxy substituted by a halogen atom, a $C_1$–$C_4$ alkyl, a carboxyl or a trifluoromethyl group; acyloxy; benzyloxy; $C_1$–$C_4$ alkylthio; phenylthio; phenylthio substituted by a halogen atom, a $C_1$–$C_4$ alkyl, a carboxyl or a trifluoromethyl group; a $C_1$–$C_4$ alkylamido; phenylamido; a radical $NR'''R^{IV}$ where $R'''$ and $R^{IV}$ are identical or different and are a $C_1$–$C_4$ alkyl or a $C_1$–$C_4$ hydroxyalkyl; a carboxyl; or a $C_1$–$C_4$ alkoxycarboxyl radical.

6. A method according to claim 1, wherein the radical $R_2$ of the formula (I) is hydrogen; chlorine; bromine; methoxy; ethoxy; phenoxy; 4-methylphenyloxy; acyloxy; benzyloxy; methylthio; ethylthio; phenylthio; 4-methylphenylthio; 2-tert-butylphenylthio; acetamido; phenylacetamido; dimethylamino; diethylamino; ethylmethylamino; or (β-hydroxyethyl)methylamino.

7. A method according to claim 6, wherein the radical $R_2$ of the formula (I) is hydrogen; chlorine; ethoxy; phenoxy; benzyloxy; acyloxy; acetamido; or dimethylamino.

8. A method according to claim 1, wherein the radicals $R_3$ and $R_4$ of the formula (I) are each independently a hydrogen atom; a linear or branched $C_1$–$C_4$ alkyl; a trifluoromethyl; a phenyl; a phenyl substituted by one or two groups selected from a halogen, a $C_1$–$C_4$ alkyl, a $C_1$–$C_4$ alkoxy, a hydroxyl, a carboxyl, a nitro group, a $C_1$–$C_4$ alkylthio, a methylenedioxy group, an amino group, a trifluoromethyl group, and a $C_1$–$C_4$ alkylamino; a benzyl radical; a benzyl radical substituted by a halogen atom, methyl, isopropyl, or methoxy; a $C_1$–$C_4$ hydroxyalkyl; a $C_1$–$C_4$ aminoalkyl; a $C_1$–$C_4$ alkylaminoalkyl; an alkoxy radical which is methoxy, ethoxy or phenoxy; methylthio; ethylthio; phenylthio; methanesulphonyl; or $R_3$ and $R_4$ together form a substituted or unsubstituted aromatic ring.

9. A method according to claim 8, wherein the radicals $R_3$ and $R_4$ of the formula (I) are each independently hydrogen; methyl; ethyl; isopropyl; n-propyl; tert-butyl; phenyl; tolyl; 2-, 3- or 4-chlorophenyl; 3- or 4-hydroxyphenyl; 3- or 4-aminophenyl; 3- or 4-methoxyphenyl; 4-trifluoromethylphenyl; benzyl; trifluoromethyl; hydroxymethyl; hydroxyethyl; hydroxyisopropyl; aminomethyl; aminoethyl; methoxy; ethoxy; methylthio; ethylthio; or $R_3$ and $R_4$ together form a phenyl ring.

10. A method according to claim 9, wherein the radicals $R_3$ and $R_4$ of the formula (I) are each independently hydrogen; methyl; ethyl; isopropyl; phenyl; 4-chlorophenyl; 4-methoxyphenyl; 4-aminophenyl; methoxy; ethoxy; methylthio; ethylthio; or $R_3$ and $R_4$ together form a phenyl ring.

11. A method according to claim 1, wherein the compound of formula (I) is:

i) a pyrazolo[1,5-b]-1,2,4-triazole of formula:

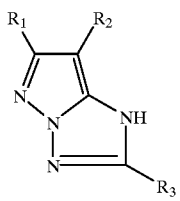

(Ia)

ii) a pyrazolo[3,2-c]-1,2,4-triazole of formula:

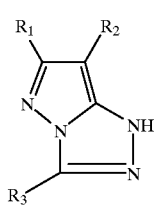

(Ib)

iii) a pyrazolotetrazole of formula:

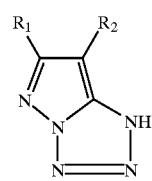

(Ic)

iv) a pyrazolo[1,5-a]imidazole of formula:

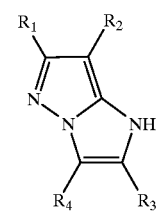

(Id)

v) a pyrazolo[5,1-e]pyrazole of formula:

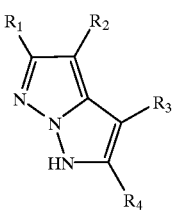

(Ie)

or vi) a pyrazolo[5,1-e]-1,2,3-triazole of formula:

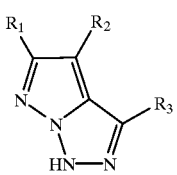

(If)

wherein $R_1$, $R_2$, $R_3$ and $R_4$ are as defined in claim 1, or an acid addition salt thereof.

12. A method according to claim 11, wherein the compound of formula (I) is formula (Ia) or (Ib), wherein:
$R_1$ is hydrogen, methyl, ethylthio, amino, trifluoromethyl, carboxyl, phenyl, ethoxy or cyano;
$R_2$ is hydrogen or chlorine; and
$R_3$ is hydrogen, methyl, ethyl, isopropyl, β-aminoethyl, β-hydroxyethyl, phenyl, methylthio or ethoxy.

13. A method according to claim 11, wherein the compound of formula (I) is formula (Ic), wherein:
$R_1$ is hydrogen, methyl, trifluoromethyl, carboxyl, phenyl, ethoxy or cyano; and
$R_2$ is hydrogen or chlorine.

14. A method according to claim 11, wherein the compound of formula (I) is formula (Id), wherein:

$R_1$ is hydrogen, methyl, trifluoromethyl, amino, carboxyl, phenyl, ethoxy or cyano;

$R_2$ is hydrogen or chlorine; and $R_3$ and $R_4$ are respectively hydrogen and hydrogen, hydrogen and methyl, methyl and hydrogen, hydrogen and amino, or hydrogen and phenyl; or together form a phenyl ring.

15. A method according to claim 11, wherein the compound of formula (I) is formula (Ie), wherein:

$R_1$ is hydrogen, methyl, trifluoromethyl, carboxyl, phenyl, ethoxy or cyano;

$R_2$ is hydrogen or chlorine; and $R_3$ and $R_4$ are respectively hydrogen and methyl, methyl and hydrogen, methyl and methyl, or hydrogen and phenyl.

16. A method according to claim 11, wherein the compound of formula (I) is formula (If) wherein:

$R_1$ is hydrogen, methyl, trifluoromethyl, carboxyl, phenyl, ethoxy or cyano;

$R_2$ is hydrogen or chlorine; and $R_3$ is hydrogen or methyl.

17. A method according to claim 11, wherein the compound is:

2-methylpyrazolo[1,5-b]-1,2,4-triazole,
2-ethylpyrazolo[1,5-b]-1,2,4-triazole,
2-isopropylpyrazolo[1,5-b]-1,2,4-triazole,
2-phenylpyrazolo[1,5-b]-1,2,4-triazole,
2,6-dimethylpyrazolo[1,5-b]-1,2,4-triazole,
6-methyl-2-ethylpyrazolo[1,5-b]-1,2,4-triazole,
6-methyl-2-isopropylpyrazolo[1,5-b]-1,2,4-triazole,
6-methyl-2-phenylpyrazolo[1,5-b]-1,2,4-triazole,
6-carboxy-2-methylpyrazolo[1,5-b]-1,2,4-triazole,
6-carboxy-2-ethylpyrazolo[1,5-b]-1,2,4-triazole,
6-carboxy-2-isopropylpyrazolo[1,5-b]-1,2,4-triazole,
6-carboxy-2-phenylpyrazolo[1,5-b]-1,2,4-triazole,
6-phenyl-2-methylpyrazolo[1,5-b]-1,2,4-triazole,
6-phenyl-2-ethylpyrazolo[1,5-b]-1,2,4-triazole,
6-phenyl-2-isopropylpyrazolo[1,5-b]-1,2,4-triazole,
6-phenyl-2-phenylpyrazolo[1,5-b]-1,2,4-triazole,
6-amino-2-methylpyrazolo[1,5-b]-1,2,4triazole,
6-amino-2-ethylpyrazolo[1,5-b]-1,2,4-triazole,
6-amino-2-isopropylpyrazolo[1,5-b]-1,2,4-triazole,
6-amino-2-phenylpyrazolo[1,5-b]-1,2,4-triazole,
6-ethylthio-2-methylpyrazolo[1,5-b]-1,2,4-triazole,
6-ethylthio-2-ethylpyrazolo[1,5-b]-1,2,4-triazole,
6-ethylthio-2isopropylpyrazolo[1,5-b]-1,2,4-triazole,
6-ethylthio-2-phenylpyrazolo[1,5-b]-1,2,4-triazole,
6-ethoxy-2-methylpyrazolo[1,5-b]-1,2,4-triazole,
6-ethoxy-2-ethylpyrazolo[1,5-b]-1,2,4triazole,
6-ethoxy-2-isopropylpyrazolo[1,5-b]-1,2,4-triazole,
6-ethoxy-2-phenylpyrazolo[1,5-b]-1,2,4-triazole,
6-methyl-2-(2'-aminoethyl)pyrazolo[1,5-b]-1,2,4-triazole,
6-carboxy-2-(2'-aminoethyl)pyrazolo[1,5-b]-1,2,4-triazole,
6-phenyl-2-(2'-aminoethyl)pyrazolo[1,5-b]-1,2,4-triazole,
6-ethylthio-2-(2'-aminoethyl)pyrazolo[1,5-b]- 1,2,4-triazole,
2-(2'-aminoethyl)pyrazolo[1,5-b]-1,2,4-triazole,
2-(2'-hydroxyethyl)pyrazolo[1,5-b]-1,2,4-triazole,
6-methyl-2-(2'-hydroxyethyl)pyrazolo[1,5-b]-1,2,4-triazole,
6-ethylthio-2-(2'-hydroxyethyl)pyrazolo[1,5-b]1,2,4-triazole,
6-carboxy-2-(2'-hydroxyethyl)pyrazolo[1,5-b]-1,2,4-triazole,
6-phenyl-2-(2'-hydroxyethyl)pyrazolo[1,5-b]-1,2,4-triazole,
7-chloro-2,6-dimethylpyrazolo[1,5-b]-1,2,4-triazole,
7-bromo-2,6-dimethylpyrazolo[1,5-b]-1,2,4-triazole,
3-methylpyrazolo[3,2c]-1,2,4-triazole,
3-methylsulphinyl-6-phenylpyrazolo[3,2-c]-1,2,4-triazole,
3-ethylpyrazolo[3,2-c]-1,2,4-triazole,
3-isopropylpyrazolo[3,2-c]-1,2,4-triazole,
3-phenylpyrazolo[3,2c]-1,2,4-triazole,
3-(2'-aminoethyl)pyrazolo[3,2-c]-1,2,4-triazole,
3-(2'-hydroxyethyl)pyrazolo[3,2-c]-1,2,4-triazole,
6-methyl-3-ethylpyrazolo[3,2-c]- 1,2,4-triazole,
3,6-dimethylpyrazolo[3,2-c]-1,2,4-triazole,
6-methyl-3-isopropylpyrazolo[3,2-c]-1,2,4-triazole,
6-methyl-3-phenylpyrazolo[3,2-c]-1,2,4-triazole,
6-methyl-3-(2'-aminoethyl)pyrazolo[3,2-c]-1,2,4-triazole,
6-methyl-3-(2'-hydroxyethyl)pyrazolo[3,2-c]-1,2,4-triazole,
6-methyl-3-methylthiopyrazolo[3,2-c]-1,2,4-triazole,
6-phenyl-3-methylpyrazolo[3,2-c]-1,2,4-triazole,
6-phenyl-3-ethylpyrazolo[3,2-c]-1,2,4-triazole,
6-phenyl-3-isopropylpyrazolo[3,2- c]-1,2,4-triazole,
6-phenyl-3-phenylpyrazolo[3,2-c]-1,2,4-triazole,
6-phenyl-3-(2'-aminoethyl)pyrazolo[3,2-c]-1,2,4-triazole,
6-phenyl-3-(2'-hydroxyethyl)pyrazolo[3,2-c]-1,2,4-triazole,
6-phenyl-3-methylthiopyrazolo[3,2-c]-1,2,4-triazole,
6-ethylthio-3-methylpyrazolo[3,2-c]-1,2,4-triazole,
6-ethylthio-3-ethylpyrazolo[3,2-c]-1,2,4-triazole,
6-ethylthio-3-isopropylpyrazolo[3,2-c]-1,2,4-triazole,
6-ethylthio-3-phenylpyrazolo[3,2-c]-1,2,4-triazole,
6-ethylthio-3-(2'-aminoethyl)pyrazolo[3,2-c]-1,2,4-triazole,
6-ethylthio-3-(2'-hydroxyethyl)pyrazolo[3,2-c]-1,2,4-triazole,
6-trifluoromethyl-3-methylthiopyrazolo[3,2-c]-1,2,4-triazole,
6-trifluoromethylpyrazolo[3,2-c]-1,2,4-triazole,
6-carboxy-3-methylpyrazolo[3,2-c]-1,2,4-triazole,
6-carboxy-3-ethylpyrazolo[3,2-c]-1,2,4-triazole,
6-carboxy-3-isopropylpyrazolo[3,2-c]-1,2,4-triazole,
6-carboxy-3-phenylpyrazolo[3,2-c]-1,2,4-triazole,
6-carboxy-3-(2'-aminoethyl)pyrazolo[3,2-c]-1,2,4-triazole,
6-carboxy-3-(2'-hydroxyethyl)pyrazolo[3,2-c]-1,2,4-triazole,
7-chloro-3,6-dimethylpyrazolo[3,2-c]-1,2,4-triazole,
7-methoxycarbonyl-3,6-dimethylpyrazolo[3,2-c]-1,2,4-triazole, pyrazolo[5,1-e]tetrazole,
6-methylpyrazolo[5,1-e]tetrazole,
6-phenylpyrazolo[5,1-e]tetrazole,
6-carboxypyrazolo[5,1-e]tetrazole,
7-chloro-6-methylpyrazolo[5,1-e]tetrazole,
pyrazolo[1,5-a]imidazole,
2-methylpyrazolo[1,5-a]imidazole,
2-phenylpyrazolo[1,5-a]imidazole,
pyrazolo[1,5-a]benzimidazole,
6-methylpyrazolo[1,5-a]imidazole,
2,6-dimethylpyrazolo[1,5-a]imidazole,
6-methyl-2-phenylpyrazolo[1,5-a]imidazole,
6-methylpyrazolo[1,5-a]benzimidazole,
6-phenylpyrazolo[1,5-a]imidazole,
6-phenyl-2-methylpyrazolo[1,5-a]imidazole,
2,6-diphenylpyrazolo[1,5-a]imidazole,
6-phenylpyrazolo[1,5-a]benzimidazole,
6-carboxypyrazolo[1,5-a]imidazole,
6-carboxy-2-methylpyrazolo[1,5-a]imidazole,
6-carboxy-2-phenylpyrazolo[1,5-a]imidazole,
6-carboxypyrazolo[1,5-a]benzimidazole,
6-ethoxypyrazolo[1,5-a]imidazole,
6-ethoxy-2-methylpyrazolo[1,5-a]imidazole,
6-ethoxy-2-phenylpyrazolo[1,5-a]imidazole,
6-trifluoromethylpyrazolo[1,5-a]benzimidazole,
6-aminopyrazolo[1,5-a]imidazole,
6-amino-2-methylpyrazolo[1,5-a]imidazole,
6-amino-2-phenylpyrazolo[1,5-a]imidazole,
6-aminopyrazolo[1,5-a]benzimidazole,
6-ethylthiopyrazolo[1,5-a]imidazole,
6-ethylthio-2-methylpyrazolo[1,5-a]imidazole,
6-ethylthio-2-phenylpyrazolo[1,5-a]imidazole,
7-chloro-6-methylpyrazolo[1,5-a]imidazole,
7-chloro-6-methylpyrazolo[1,5-a]benzimidazole,
8-amino-4-methylpyrazolo[5,1-e]pyrazole,
8-amino-5-chloro-4-methylpyrazolo[5,1-e]pyrazole,
5-methylpyrazolo[5,1-e]-1,2,3-triazole,
5-methyl-6-chloropyrazolo[5,1-e]-1,2,3-triazole,
5-phenylpyrazolo[5,1-e]-1,2,3-triazole, or an acid addition salt thereof.

18. A method according to claim 1, wherein the compound of formula I is:

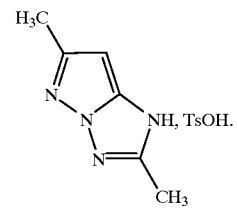

19. A method according to claim 1, wherein the compound of formula (I) is a hydrochloride, hydrobromide, sulphate, tartrate, benzenesulphonate, lactate, tosylate, or acetate acid addition salt.

20. A method according to claim 1, wherein the compound of formula (I) represents from about 0.0005 to about 12% by weight of the total weight of the dyeing composition.

21. A method according to claim 20, wherein the compound of formula (I) represents from about 0.005 to about 6% by weight of the total weight of the dyeing composition.

22. A method according to claim 1, wherein the oxidation base represents from about 0.0005 to about 12% by weight of the total weight of the dyeing composition.

23. A method according to claim 22, wherein the oxidation base represents from about 0.005 to about 6% by weight of the total weight of the dyeing composition.

24. A method according to claim 1, further comprising at least one additional coupler other than a compound of formula (I), at least one direct dye or at least one of each.

25. A method according to claim 1, wherein the medium suitable for dyeing comprises water or a mixture of water and an organic solvent.

26. A method according to claim 25, wherein the medium suitable for dyeing comprises a mixture of water and an organic solvent which is a lower $C_1$–$C_4$ alcohol, glycerol, glycol, glycol ether, aromatic alcohol, or a mixture thereof.

27. A method according to claim 1, wherein said composition has a pH of from about 3 to about 12.

28. A method according to claim 1, wherein the composition is the form of a liquid, cream, or gel.

29. A method according to claim 1, wherein the keratin fiber is human hair.

30. A method according to claim 1, wherein the oxidizing agent is hydrogen peroxide, urea peroxide, an alkali metal bromate, or a persalt.

31. A method according to claim 30, wherein the oxidizing agent is a persalt, and further wherein said persalt is a perborate or persulphate.

32. A method according to claim 1, wherein the at least one oxidation base is a para-phenylenediamine, a bis-phenylalkylenediamine, a para-aminophenol, an ortho-aminophenol, a heterocyclic base, or an acid addition salt thereof.

* * * * *

UNITED STATES PATENT AND TRADEMARK OFFICE
CERTIFICATE OF CORRECTION

PATENT NO. : 6,231,623 B1
DATED : May 15, 2001
INVENTOR(S) : Vidal et al.

Page 1 of 1

It is certified that error appears in the above-identified patent and that said Letters Patent is hereby corrected as shown below:

Column 22, claim 1,
Line 14, change "find" to -- and --.

Column 24, claim 11,
Line 16, change "(1d)" to -- (Id) --;
Line 30, change "(1e)" to -- (Ie) --;
Line 45, change "(1f)" to -- (If) --.

Column 25, claim 17,
Line 45, change "1, 2, 4 triazole" to -- 1, 2, 4-triazole --.

Signed and Sealed this

Thirteenth Day of November, 2001

Attest:

*Attesting Officer*

NICHOLAS P. GODICI
*Acting Director of the United States Patent and Trademark Office*